United States Patent [19]
Rabinovich et al.

[11] Patent Number: 5,749,369
[45] Date of Patent: May 12, 1998

[54] METHOD AND DEVICE FOR STABLE IMPEDANCE PLETHYSMOGRAPHY

[75] Inventors: Pavel Rabinovich, Jerusalem; Michael Shochat, Matan; Vladimir Zeldin; Oscar Milman, both of Maale Adumim, all of Israel

[73] Assignee: R.S. Medical Monitoring Ltd., Jerusalem, Israel

[21] Appl. No.: 820,464

[22] Filed: Mar. 17, 1997

Related U.S. Application Data

[63] Continuation of Ser. No. 693,660, Aug. 9, 1996.
[51] Int. Cl.$^6$ .................................................... A61B 5/05
[52] U.S. Cl. ................................. 128/734; 128/723
[58] Field of Search ................................. 128/734, 735, 128/693, 723

[56] References Cited

U.S. PATENT DOCUMENTS

| | | |
|---|---|---|
| Re. 30,101 | 9/1979 | Kubicek et al. |
| 3,750,649 | 8/1973 | Severinghaus. |
| 3,789,834 | 2/1974 | Duroux. |
| 3,851,641 | 12/1974 | Toole et al. |
| 3,871,359 | 3/1975 | Pacela. |
| 3,874,368 | 4/1975 | Asrican. |
| 3,971,365 | 7/1976 | Smith. |
| 4,078,553 | 3/1978 | Duroux. |
| 4,116,231 | 9/1978 | Matsuo. |
| 4,240,445 | 12/1980 | Iskander et al. |
| 4,269,195 | 5/1981 | Itoh. |
| 4,486,835 | 12/1984 | Bai et al. |

(List continued on next page.)

FOREIGN PATENT DOCUMENTS

WO 86/03391 6/1986 WIPO.

OTHER PUBLICATIONS

Luepker et al, "Transthoracic electrical impedance: Quantitative evaluation of a non-invasive measure of thoracic fluid volume", *Am. Heart J.*, vol. 85, No. 1, pp. 83–93 (1973).

Berman, et al, "Transthoracic Electrical Impedance as a Guide to Intravascular Overload", *Arch. Of Surg.*, vol. 102, pp. –61–64, (1971).

Staub, N.C., "Clinical Use of Lung Water Measurements", *Chest*, 90 (4), pp. 588–594, (1986).

Staub, et al, "Conference report of a workshop on the measurement of lung water", *Critical Care Mag.*, 8(12), pp. 752–759, (1980).

Miniati et al, "Detection of Lung edema", *Critical Care Mag.*, 15(12), pp. 1146–1154 (1987).

Fein et al, "Evaluation of Transthoracic Electrical Impedance in the Diagnosis of Pulmonary Edema", *Circulation*, 60(5), pp. 1156–1160, (1979).

*Primary Examiner*—Francis Jaworski
*Attorney, Agent, or Firm*—Mark M. Friedman

[57] ABSTRACT

A method and device for impedance plethysmography, with relative immunity to skin-electrode contact resistance drift are provided. The method comprises: (a) placing: (i) first and second measurement electrodes on a biological object; (ii) first and second reference electrodes on opposite sides of the first measurement electrode; and (iii) third and fourth reference electrodes on opposite sides of the second measurement electrode, so as to define a measurement electrical circuit and six reference electrical circuits; (b) measuring: (i) a first electrical impedance of the measurement circuit; (ii) a second, third and fourth electrical impedances of three reference circuits which include the first measurement electrode, the first reference electrode and the second reference electrode; (iii) a fifth, sixth and seventh electrical impedances of three reference circuits which include the second measurement electrode, the third reference electrode and the fourth reference electrode; (c) calculating: (i) the skin-electrode resistance drift of the first measurement electrode based on the second, third and fourth electrical impedances; (ii) the skin-electrode resistance drift of the second measurement electrode based on the fifth, sixth and seventh electrical impedances; and (d) calculating the internal impedance of the biological object by subtracting the skin-electrode resistance drifts of the first and second measurement electrodes from the first electrical impedance.

23 Claims, 9 Drawing Sheets

U.S. PATENT DOCUMENTS

| | | | |
|---|---|---|---|
| 4,561,448 | 12/1985 | Buchas | 128/734 |
| 4,649,932 | 3/1987 | Smith . | |
| 4,690,149 | 9/1987 | Ko . | |
| 4,823,797 | 4/1989 | Heinze et al. . | |
| 5,465,730 | 11/1995 | Zadehkoochak et al. . | |
| 5,501,230 | 3/1996 | Laribiere . | |

METHOD AND DEVICE FOR STABLE IMPEDANCE PLETHYSMOGRAPHY

This is a continuation in part of U.S. patent application Ser. No. 08/693,660, filed Aug. 9 1996.

FIELD AND BACKGROUND OF THE INVENTION

The present invention relates to noninvasive medical monitoring systems and, more particularly, to a method and device for monitoring the change in time of the internal electrical impedance of a portion of a living body, such as the lungs or the brain, the method and the device being characterized by relative immunity to drift of skin-to-electrode impedance.

Fluid buildup is associated with many diseases, notably diseases of the heart. An important example of fluid buildup associated with heart disease is acute edema of the lungs. Because these fluids are electrically conductive, changes in their volume can be detected by the technique of impedance plethysmography, in which the electrical impedance of a part of the body is measured by imposing an electrical current across the body and measuring the associated voltage difference. For example, experiments with dogs (R. V. Luepker et al., American Heart Journal, Vol.85, No. 1, pp 83–93, January 1973) have shown a clear relationship between the transthoracic electrical impedance and the change in pulmonary fluid volume.

The monitoring of the amount of liquid within a biological object using two electrodes, one either side of the biological object, is well known in the art. However, this method has proved to be unfit for prolonged monitoring due to the drift of skin-to-electrode contact layer resistance. This drift is due to ions from sweat and skin penetrating the electrolytic paste of the electrode, and the wetting of the epidermis, over the course of several hours. A method for overcoming this problem was developed by Kubicek et al. (Annals of the New York Academy of Sciences, 1970, 170(2):724–32; U.S. Pat. No. 3,340,867, reissued as Re. 30,101). Related U.S. patents include Asrican (U.S. Pat. No. 3,874,368), Smith (U.S. Pat. No. 3,971,365), Matsuo (U.S. Pat. No. 4,116,231) and Itoh (U.S. Pat. No. 4,269,195). The method of Kubicek et al. uses a tetrapolar electrode system whereby the outer electrodes establish a current field through the chest. The inner voltage pickup electrodes are placed as accurately as is clinically possible at the base of the neck and at the level of the diaphragm. This method regards the entire portion of the chest between the electrodes as a solid cylinder with uniform parallel current fields passing through it. However, because this system measures the impedance of the entire chest, and because a large part of the electrical field is concentrated in the surface tissues, this method is not sufficiently specific for measuring liquid levels in the lungs and has low sensitivity: 50 ml per Kg of body weight (Y. R. Berman, W. L. Schutz, Archives of Surgery, 1971. V. 102:61–64). It should be noted that such sensitivity has proved to be insufficient for obtaining a significant difference between impedance values in patients without pulmonary edema to those with an edema of average severity (A. Fein et al., Circulation, 1979,60(5):1156–60). In their report on the conference in 1979 concerning measuring the change in the amount of liquid in the lungs (Critical Care Medicine, 1980,8(12):752–9), N. C. Staub and J. C. Hogg summarize the discussion on the reports concerning the reports on the method of Kubicek et al. for measuring thoracic bio-impedance. They conclude that the boundaries of the normal values are too wide, and the sensitivity of the method is lower than the possibilities of clinical observation and radiological analysis, even when the edema is considered to be severe. It is indicative that, in a paper six years later by N. C. Staub (Chest. 1986,90(4):588–94), this method is not mentioned at all. Other problems with this method include the burdensome nature of the two electrodes tightly attached to the neck, and the influence of motion artifacts on the impedance readings received.

Another method for measuring liquid volume in the lungs is the focussing electrode bridge method of Severinghaus (U.S. Pat. No. 3,750,649). This method uses two electrodes located either side of the thorax, on the left and right axillary regions. Severinghaus believed that part of the electrical field was concentrated in surface tissues around the thorax and therefore designed special electrodes to focus the field through the thorax. This method does not solve the problems associated with the drift in the skin-to-electrode resistance described above. An additional problem is the cumbersome nature of the large electrodes required. It is indicative that the article by Staub and Hogg, describing the 1979 conference, mentions that the focussing bridge transthoracic electrical impedance device was not discussed, despite the presence of its developer at the conference. A review by M. Miniati et al. (Critical Care Medicine, 1987,15(12):1146–54) characterizes both the method of Kubicek et al. and the method of Severinghaus as "insufficiently sensitive, accurate, and reproducible to be used successfully in the clinical setting" (p. 1146).

Toole et al., in U.S. Pat. No. 3,851,641, addresses the issue of electrode drift by measuring the impedance at two different frequencies. However, their method is based on a simplified equivalent circuit for the body in which the resistances and capacitances are assumed to be independent of frequency. Pacela, in U.S. Pat. No. 3,871,359, implicitly addresses the issue of electrode drift by measuring two impedances across two presumably equivalent parts of a body, for example, a right and a left arm or a right and a left leg, and monitoring the ratio between the two impedances. His method is not suitable for the monitoring of organs such as the lungs, which are not symmetric, or the brain, of which the body has only one. Other notable recent work in measuring the impedance of a portion of the body includes the tomographic methods and apparatuses of Bai et al. (U.S. Pat. No. 4,486,835) and Zadehkoochak et al. (U.S. Pat. No. 5,465,730). In the form described, however, tomographic methods are based on relatively instantaneous measurements, and therefore are not affected by electrode drift. If tomographic methods were to be used for long-term monitoring of pulmonary edema, they would be as subject to problems of skin-to-electrode impedance drift as the other prior art methods.

There is thus a widely recognized need for, and it would be highly advantageous to have, a method and device for impedance plethysmography that is relatively immune to electrode drift over an extended period of time.

SUMMARY OF THE INVENTION

According to the present invention there is provided a method for monitoring the internal electrical impedance of a biological object, with compensation for skin-to-electrode resistance drift, during an extended monitoring period, comprising the steps of: (a) placing a first electrode and a second electrode on the biological object, the first electrode and the second electrode being part of a measurement circuit; (b) placing a third electrode on the biological object, substantially adjacent to the first electrode, the first electrode and the third electrode being part of a reference circuit; (c) at least twice during the monitoring period: (i) measuring a first electrical impedance of the measurement circuit, and (ii) measuring a second electrical impedance of the reference circuit.

According to the present invention there is provided a method for monitoring the internal electrical impedance of a biological object, with compensation for skin-electrode resistance drift, during an extended monitoring period, comprising the steps of: (a) placing a first electrode and a second electrode on the biological object, the first electrode and the second electrode being part of a measurement circuit; (b) placing a third electrode on the biological object, substantially adjacent to the first electrode, the first electrode and the third electrode being part of a reference circuit; (c) imposing an alternating electrical current between the first electrode and the second electrode; (d) imposing the alternating electrical current between the first electrode and the third electrode; and (e) at least twice during the monitoring period: (i) obtaining a first voltage signal representative of a voltage difference in the measurement circuit, and (ii) obtaining a second voltage signal representative of a voltage difference in the reference circuit.

According to the present invention there is provided an impedance plethysmography device, comprising: (a) a first electrode; (b) a second electrode; (c) a third electrode; (d) a measurement electrical circuit including the first electrode, the second electrode, and a first impedance measurement means for measuring a first electrical impedance; and (e) a reference electrical circuit including the first electrode, the third electrode, and a second impedance measurement means for measuring a second electrical impedance.

According to the present invention there is provided a medical monitoring system comprising an impedance plethysmography device, the impedance plethysmography device further comprising: (a) a first electrode; (b) a second electrode; (c) a third electrode; (d) a measurement electrical circuit including the first electrode, the second electrode, and a first impedance measurement means for measuring a first electrical impedance; and (e) a reference electrical circuit including the first electrode, the third electrode, and a second impedance measurement means for measuring a second electrical impedance.

The present invention is a method and device for monitoring the electrical impedance of a biological object such as a living body for an extended period of time, where the term "extended" is used herein to mean at least as long as the time over which skin-to-electrode resistance drift changes the skin-to-electrode resistance by an amount comparable to the anticipated change in the impedance of the biological object itself. Examples of the use of the invention in a hospital setting include the monitoring of pulmonary edema and cerebral edema. Fluid builds up in the lungs and brain, respectively, to a level detectable by the present invention sooner than clinical symptoms appear. Therefore, a patient to whom the device of the present invention is attached may be monitored remotely for pulmonary edema or cerebral edema, and appropriate therapies may be initiated much earlier than if only clinical symptoms are relied on, with a consequent reduction of mortality and morbidity.

The present invention is based on two physical assumptions. The first assumption is that the total impedance measured across two electrodes placed on opposite sides of the biological object is the sum of two impedances: the impedance of the skin-electrode contacts and the internal impedance of the body. The second assumption is that all skin-electrode contacts drift to the same degree in the same amount of time. According to the present invention, two measurement electrodes are placed on opposite sides of the biological object, and a third, reference electrode is placed next to one of the measurement electrodes. The total impedance measured between the measurement electrodes is a sum of the internal impedance of the biological object and skin-electrode contacts impedances. The impedance measured between the reference electrode and the adjacent measurement electrode is substantially only the skin-electrode contacts impedances and the skin impedance. Therefore, subtracting the impedance measured between the reference electrode and the adjacent measurement electrode from the impedance measured between the two measurement electrodes yields a corrected impedance whose change over time accurately reflects the change over time of the internal impedance of the biological object. A persistent decrease in the corrected impedance may be indicative of a buildup of electrically conductive fluid in the body.

Reference electrodes have been used before in a biomedical context, notably by Laribiere (U.S. Pat. No. 5,501,230). However, Laribiere uses a reference electrode for a purpose different from its use in the present invention. Laribiere's reference electrode is used in a circuit that detects when one of two signal measuring electrodes becomes detached from the skin of a patient.

Most conveniently, the impedance measurements of the present invention are performed by imposing alternating current on the measurement circuit (the circuit that includes the two measurement electrodes) and the reference circuit (the circuit that includes the reference electrode and the adjacent measurement electrode), preferably by using two different electrical sources of an identical current intensity. Because both circuits have the same current, voltage drops measured between the electrodes serve as proxies for the impedances themselves. Preferably, a balancing means is provided to equalize the voltage drops across the two circuits at the beginning of a monitoring period. This balancing means may be a variable resistor in series with the electrodes in the reference circuit. At the beginning of a monitoring period, the balancing means is adjusted so that the voltage drops across the two circuits are substantially equal. Since the impedance changes of the skin-electrode contacts of the all the electrodes are assumed to be substantially identical, any change in the voltage drop across the measurement circuit with relation to the reference circuit indicates a change in the internal electrical impedance of the biological object, and therefore a change in the liquid volume within the biological object. As fluid builds up, the difference between the two voltage drops increases. When this difference exceeds a threshold, an emergency condition is signalled, for example by an audible alarm.

The principle underlying such configuration is that skin-to-electrodes resistance drifts occur to the same amount both in the measurement circuit and the reference circuit, so that the balance between these circuits remains undisturbed. A change in the balance between the measurement circuit and the reference circuit is only possible when the internal impedance of the biological object changes owing to changes in the amount of liquid within the biological object.

In other embodiments of the present invention, the balancing means is not used. Instead, signal processing circuitry is provided that digitizes the voltage drops, subtracts the voltage drop across the reference circuit from the voltage drop across the measurement circuit, and, at the beginning of a monitoring period, stores the initial value of that difference. That initial value is subtracted from subsequently measured values of that difference to provide a second difference. When the second difference exceeds a threshold, an emergency condition is signalled.

The scope of the present invention includes the device of the present invention both as an independent device and as a component of a more general medical monitoring system. Such a monitoring system may also include a pulmonary monitor or an ECG.

According to another preferred embodiment, a method and device according to the present invention make it possible to accurately calculate the value of the internal electrical impedance of the biological object by calculating skin-electrode resistance of each of the measurement electrodes. Such embodiment makes it possible to carry out long-term monitoring of the internal electrical impedance of the biological object even when the impedance values of the skin-electrode contacts of the measurement electrodes are substantially different.

Thus, a method according to the present invention comprises the steps of: (a) placing a first measurement electrode and a second measurement electrode on the biological object, the first measurement electrode and the second measurement electrode being part of a measurement circuit; (b) placing a first reference electrode and a second reference electrode on the biological object, substantially adjacent to the first measurement electrode, the first measurement electrode and the first reference electrode being part of a first reference circuit, the first measurement electrode and the second reference electrode being part of a second reference circuit, the first reference electrode and the second reference electrode being part of a third reference circuit; (c) at least once during the monitoring period: (i) measuring a first electrical impedance of the measurement circuit; (ii) measuring a second electrical impedance of the first reference circuit; (iii) measuring a third electrical impedance of the second reference circuit; and (iv) measuring a fourth electrical impedance of the third reference circuit.

Preferably, a method according to the present invention further comprises the steps of: (a) placing a third reference electrode and a fourth reference electrode on the biological object, substantially adjacent to the second measurement electrode, the second measurement electrode and the third reference electrode being part of a fourth reference circuit, the second measurement electrode and the fourth reference electrode being part of a fifth reference circuit, the third reference electrode and the fourth reference electrode being part of a sixth reference circuit; (b) at least once during the monitoring period: (i) measuring a fifth electrical impedance of the fourth reference circuit; (ii) measuring a sixth electrical impedance of the fifth reference circuit; and (iii) measuring a seventh electrical impedance of the sixth reference circuit.

Preferably, the first reference electrode and the second reference electrode are placed on opposite sides of the first measurement electrode.

At least once during the monitoring period, the value of the skin-electrode resistance of the first measurement electrode is calculated according to:

$$Z_1 = (Z_I + Z_{II} - Z_{III})/2$$

where:

$Z_1$ is the skin-electrode resistance of the first measurement electrode;

$Z_I$ is the second electrical impedance;

$Z_{II}$ is the third electrical impedance; and $Z_{III}$ is the fourth electrical impedance.

Preferably, the third reference electrode and the fourth reference electrode are placed on opposite sides of the second measurement electrode.

At least once during the monitoring period, the value of the skin-electrode resistance of said second measurement electrode is calculated according to:

$$Z_2 = (Z_{IV} + Z_V - Z_{VI})/2$$

where:

$Z_2$ is the skin-electrode resistance of the second measurement electrode;

$Z_{IV}$ is the fifth electrical impedance;

$Z_V$ is the sixth electrical impedance; and $Z_{VI}$ is the seventh electrical impedance.

At least once during the monitoring period, the internal electrical impedance of the biological object is calculated according to:

$$Z_{IN} = Z_T - (Z_1 + Z_2)$$

where:

$Z_{IN}$ is the internal electrical impedance of the biological object;

$Z_1$ is the skin-electrode resistance of the first measurement electrode;

$Z_2$ is the skin-electrode resistance of the second measurement electrode; and $Z_T$ is the first electrical impedance.

Preferably, the method further comprises the step of: if the internal electrical impedance of the biological object decreases below a minimum threshold value, an emergency procedure is initiated. Preferably, the method further comprises the step of: if the internal electrical impedance of the biological object increases above a maximum threshold value, an emergency procedure is initiated.

When the electrical impedance of the biological object is calculated at least twice during the monitoring period, the method may further comprise the step of: if the change in the internal electrical impedance of the biological object exceeds a threshold value, an emergency procedure is initiated.

According to the present invention there is provided a method for monitoring the internal electrical impedance of a biological object, with compensation for skin-electrode resistance drift, during an extended monitoring period, comprising the steps of: (a) placing a first measurement electrode and a second measurement electrode on the biological object, the first measurement electrode and the second measurement electrode being part of a measurement circuit; (b) placing a first reference electrode and a second reference electrode on the biological object, substantially adjacent to the first measurement electrode, the first measurement electrode and the first reference electrode being part of a first reference circuit, the first measurement electrode and the second reference electrode being part of a second reference circuit, the first reference electrode and the second reference electrode being part of a third reference circuit; (c) at least once during the monitoring period: (i) imposing an alternating electrical current between the first measurement electrode and the second measurement electrode and obtaining a first voltage signal representative of a voltage drop in the measurement circuit; (ii) imposing an alternating electrical current between the first measurement electrode and the first reference electrode and obtaining a second voltage signal representative of a voltage drop in the first reference circuit; (iii) imposing an alternating electrical current between the first measurement electrode and the second reference electrode and obtaining a third voltage signal representative of a voltage drop in the second reference circuit; (iv) imposing an alternating electrical current between the first reference electrode and the second reference electrode and obtaining a fourth voltage signal representative of a voltage drop in the third reference circuit.

Preferably, a method according to the present invention further comprises the steps of: (a) placing a third reference electrode and a fourth reference electrode on the biological object, substantially adjacent to the second measurement electrode, the second measurement electrode and the third reference electrode being part of a fourth reference circuit, the second measurement electrode and the fourth reference electrode being part of a fifth reference circuit, the third reference electrode and the fourth reference electrode being part of a sixth reference circuit; (b) at least once during the monitoring period: (i) imposing an alternating electrical current between the second measurement electrode and the third reference electrode and obtaining a fifth voltage signal representative of a voltage drop in the fourth reference circuit; (ii) imposing an alternating electrical current between the second measurement electrode and the fourth reference electrode and obtaining a sixth voltage signal representative of a voltage drop in the fifth reference circuit; and (iii) imposing an alternating electrical current between the third reference electrode and the fourth reference electrode and obtaining a seventh voltage signal representative of a voltage drop in the sixth reference circuit.

According to the present invention there is provided an impedance plethysmography device, comprising: (a) a first measurement electrode; (b) a second measurement electrode; (c) a first reference electrode; (d) a second reference electrode; (e) a measurement electrical circuit including the first measurement electrode, the second measurement electrode, and a first impedance measurement means for measuring a first electrical impedance; (f) a first reference electrical circuit including the first measurement electrode, the first reference electrode, and a second impedance measurement means for measuring a second electrical impedance; (g) a second reference electrical circuit including the first measurement electrode, the second reference electrode, and a third impedance measurement means for measuring a third electrical impedance; and (h) a third reference electrical circuit including the first reference electrode, the second reference electrode, and a fourth impedance measurement means for measuring a fourth electrical impedance;

Preferably, a device according to the present invention further comprises: (a) a third reference electrode; (b) a fourth reference electrode; (c) a fourth reference electrical circuit including the second measurement electrode, the third reference electrode, and a fifth impedance measurement means for measuring a fifth electrical impedance; (d) a fifth reference electrical circuit including the second measurement electrode, the fourth reference electrode, and a sixth impedance measurement means for measuring a sixth electrical impedance; (e) a sixth reference electrical circuit including the third reference electrode, the fourth reference electrode, and a seventh impedance measurement means for measuring a seventh electrical impedance.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method and device for monitoring the electrical impedance of a living body. Specifically, the present invention can be used to monitor a patient for signs of edema, for example pulmonary edema or cerebral edema.

The principles and operation of a monitoring system according to the present invention may be better understood with reference to the drawings and the accompanying description.

Figure 1:
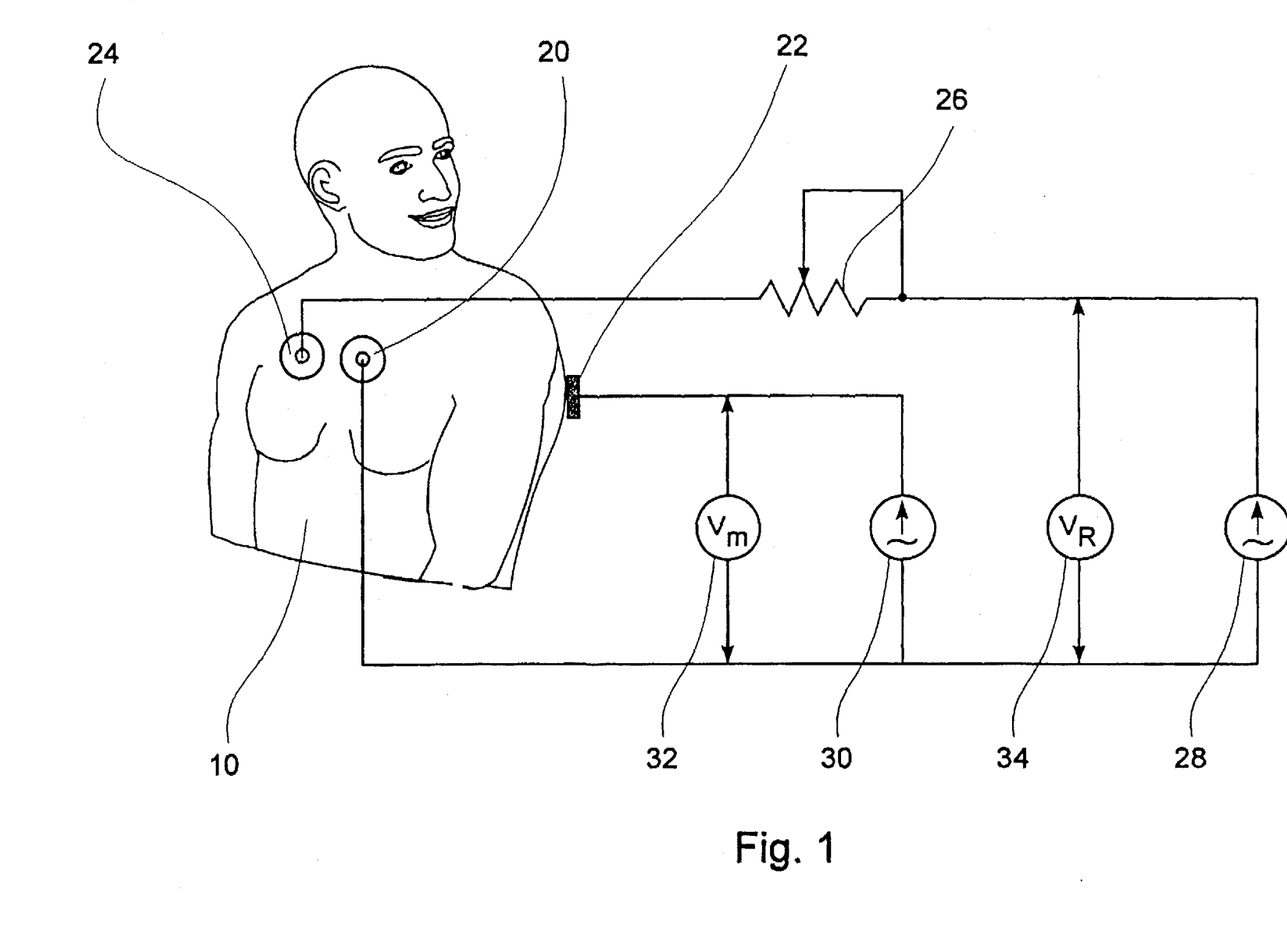
FIG. 1 is a schematic illustration of a preferred embodiment of a device of the present invention as used to monitor pulmonary edema.

Referring now to the drawings, FIG. 1 illustrates the circuitry of a preferred embodiment of a device of the present invention as used to monitor pulmonary edema. A first measurement electrode 20 and a second measurement electrode 22 are placed on opposite sides of the thorax of a patient 10. Electrode 20 is placed at the point of intersection of the 4-intercostal space and the medroclavicular line of patient 10. Electrode 22 is placed on the back of patient 10, opposite electrode 20. A reference electrode 24 is placed on the thorax of patient 10 close to electrode 20. Preferably, sources 28 and 30 of alternating current supply electrical current of an identical intensity to the electrodes as shown. Preferably, sources 28 and 30 supply between about 1 mA and about 2 mA of current at a frequency of between about 50 Khz and about 200 Khz. The term "frequency", as used herein, refers to the fundamental frequency of a periodic waveform, so that the scope of the present invention includes alternating current of any periodic waveform, for example square waves, and not just sinusoidally alternating current. A variable resistor 26 is in series with reference electrode 24. Patient 10, electrodes 20 and 22, and current source 30 comprise a measurement circuit. Patient 10, electrodes 20 and 24, variable resistor 26, and current source 28 comprise a reference circuit. Voltage measurement means 32 and 34 are provided for measuring the voltage drop $V_M$ across the measurement circuit (which is proportional to the total impedance of the biological object), and the voltage drop $V_R$ across the reference circuit, respectively.

When using the embodiment shown in FIG. 1, an assumption is made that the impedance values of the skin-electrode contacts of electrodes 20, 22 and 24 are substantially identical at a given time. Thus, any change in the total impedance of the biological object (which is indicated by $V_M$) with relation to the impedance of the reference circuit (which is indicated by $V_R$) is attributed to changes in the internal impedance of the biological object.

It is to be understood that the preferred embodiment of FIG. 1 is illustrative. In particular, the scope of the present invention is not restricted to circuitry in which voltage drops across the measurement circuit and the reference circuit are measured explicitly, but rather includes all circuitry which accomplishes the ends of the method of the present invention, using signals representative of the voltage drops $V_M$ and $V_R$.

Preferably, at the beginning of a monitoring session, variable resistor 26 is adjusted so that $V_M$ and $V_R$ are substantially equal. Subsequently, $V_M$ and $V_R$ are monitored periodically, preferably automatically. Since the impedance changes of the skin-electrode contacts of electrodes 20, 22, and 24 are assumed to be substantially identical, any substantial change of $V_M$ with relation to $V_R$ indicates a change in the internal electrical impedance of the thorax of patient 10. Thus, a drop of the internal electrical impedance of the thorax of patient 10 indicates the onset of pulmonary edema in the patient. Such a method is advantageous since it makes it possible to diagnose pulmonary edema even when the impedance changes of the skin-electrode contacts of electrodes 20 and 22 are substantially greater than the change in the internal impedance of the thorax of patient 10.

Figure 2:
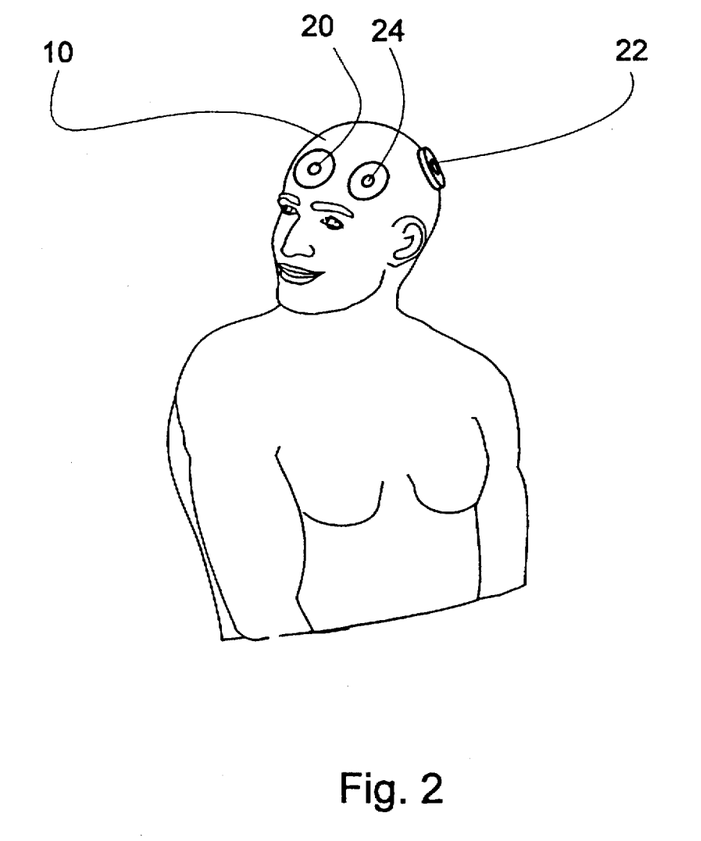
FIG. 2 is a partial schematic illustration of the use of the device shown in FIG. 1 as used to monitor cerebral edema.

FIG. 2 shows how electrodes 20, 22, and 24 are placed on the head of patient 10 for monitoring cerebral edema. Measurement electrodes 20 and 22 are placed on opposite sides of the head of patient 10, and reference electrode 24 is placed next to electrode 20. Electrodes 20, 22, and 24 are connected to the circuitry of the device of the present invention just as in the monitoring of pulmonary edema depicted in FIG. 1.

Figure 3:
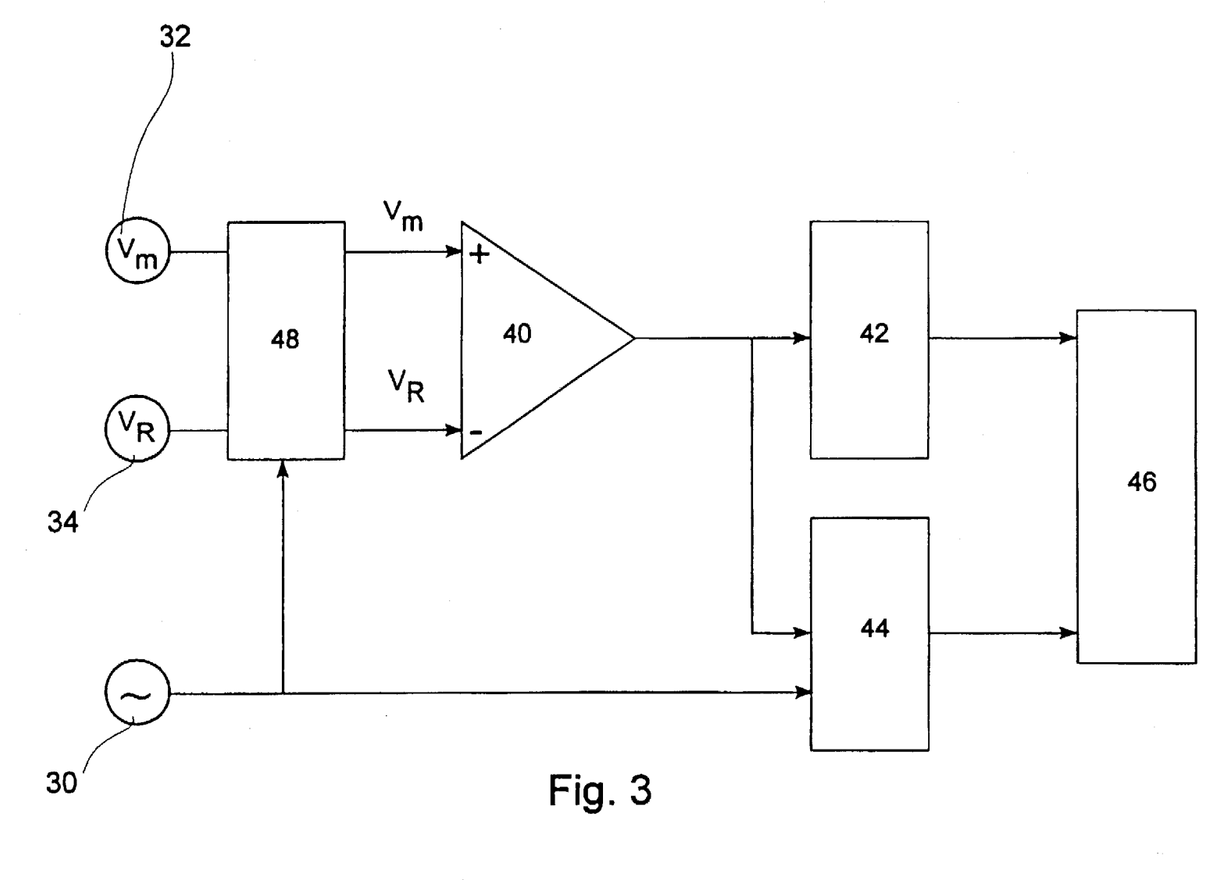
FIG. 3 is a schematic block diagram of the signal processing in a preferred embodiment of the device shown in FIG. 1.

FIG. 3 is a schematic block diagram of the signal processing in an exemplary embodiment of the present invention. A signal from voltage measurement means 32 representing $V_R$ is phase locked with a signal from voltage measurement means 34 representing $V_M$ and with a signal from current source 30 in a suitable phase lock means 48. Thus, phase lock means 48 equalizes the phases of the signals representing $V_M$ and $V_R$ to the phase of the signal from current source 30. The signal representing $V_M$ then is subtracted from the signal representing $V_R$ in a suitable subtraction means 40, for example, an operational amplifier, to provide a difference signal. This difference signal is input to an amplitude measurement means 42 and a phase detection means 44. Amplitude measurement means 42 measures the amplitude of the difference signal. Phase detection means 44 measures the phase difference between the difference signal and a reference signal from current source 30. The amplitude and the phase difference are input to a display means 46, which displays the values of the amplitude of the difference signal and its phase relative to current source 30.

Figure 4A:
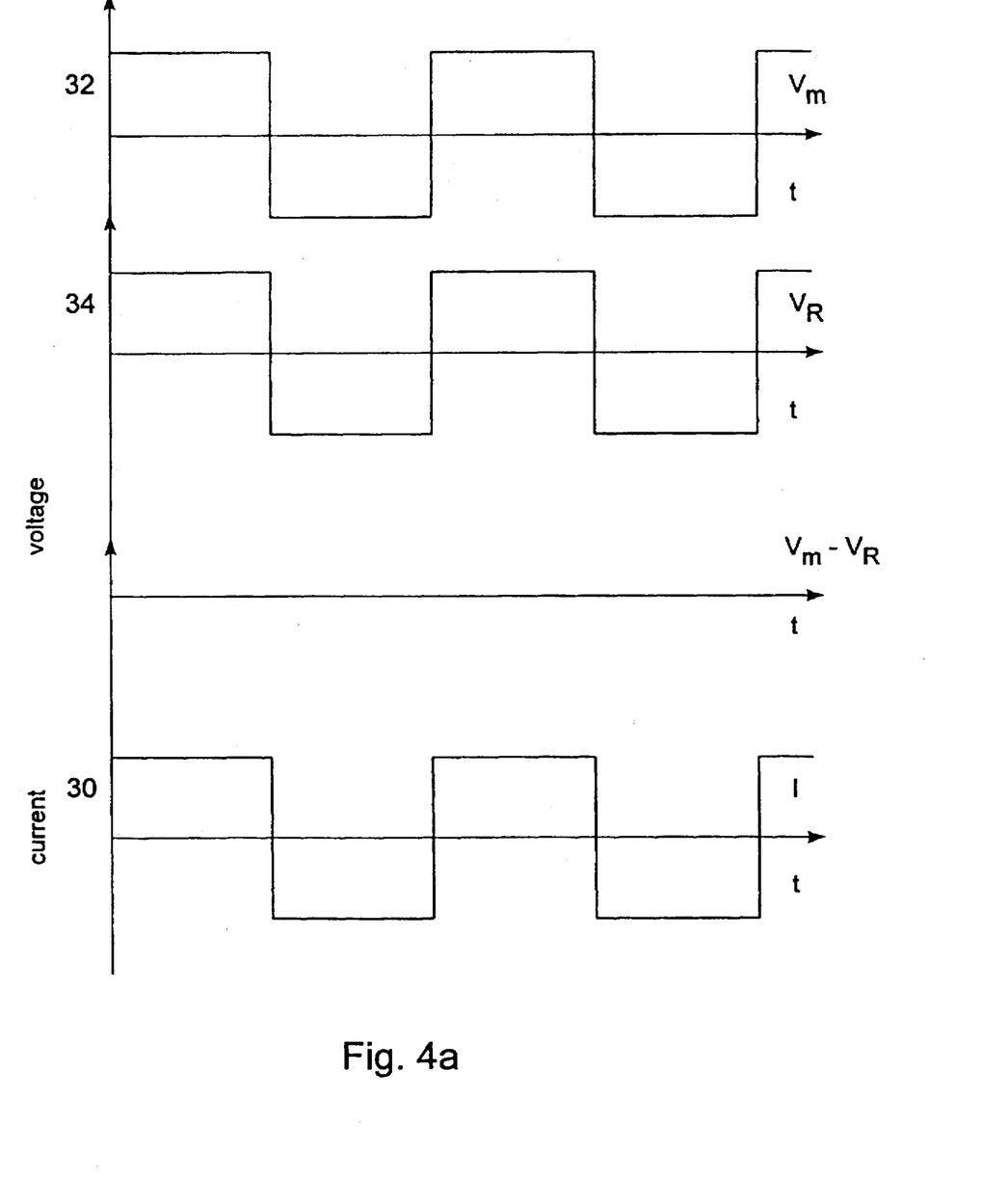
FIG. 4A is a schematic plot of the voltages and the current at the start of monitoring.
Figure 4B:
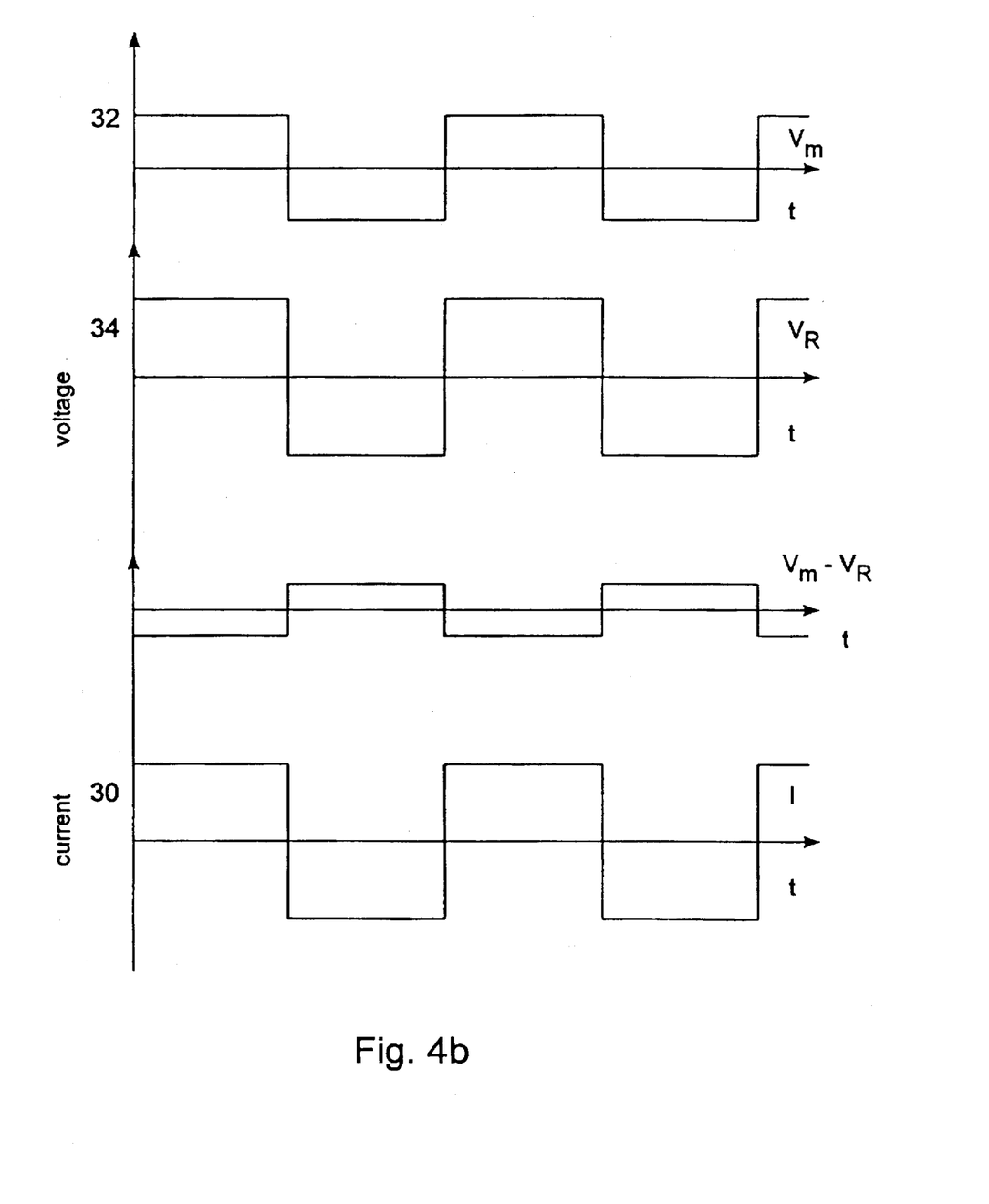
FIG. 4B is a schematic plot of the voltages and the current at the onset of significant fluid buildup.
Figure 4C:
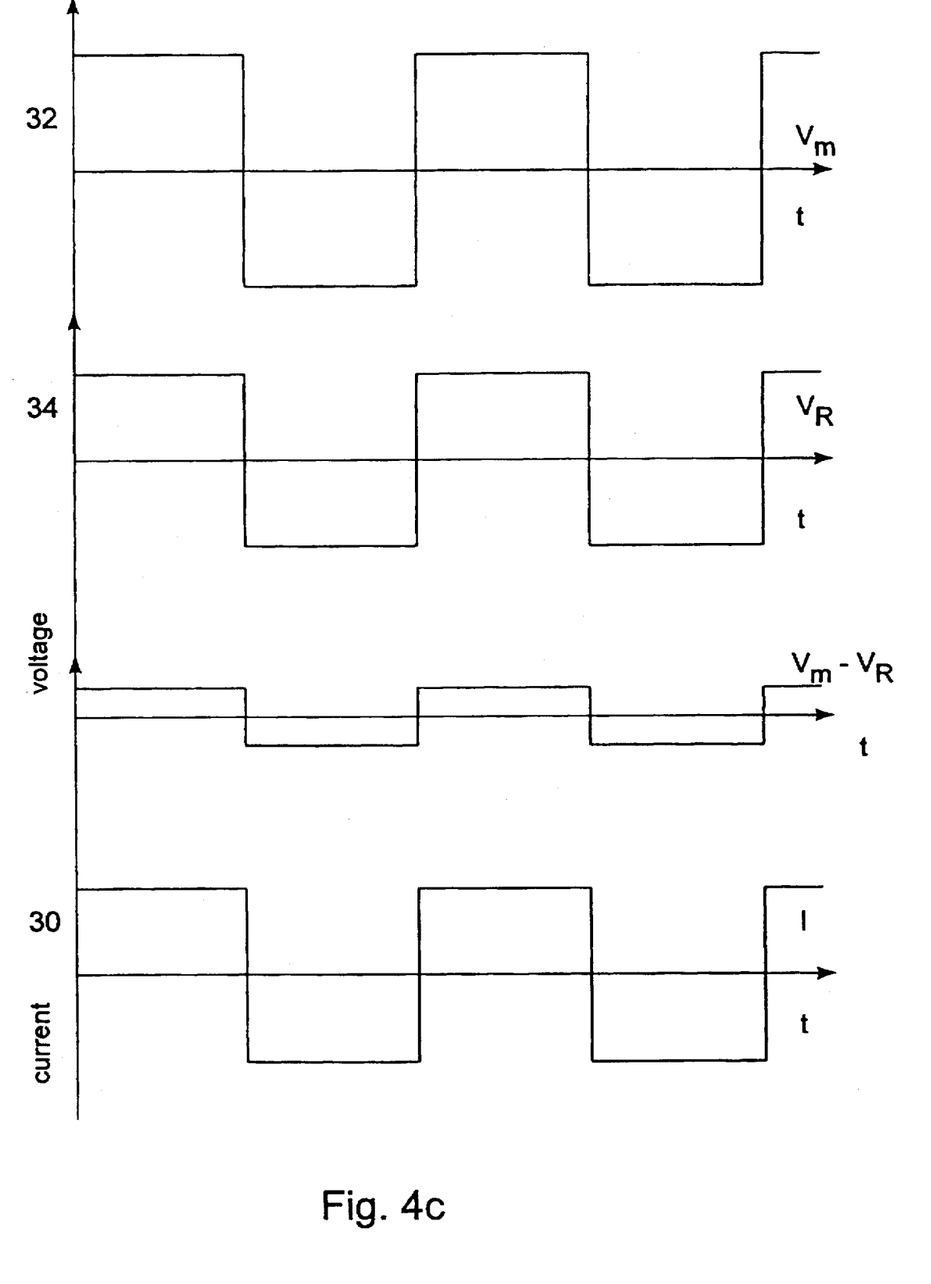
FIG. 4C is a schematic plot of the voltages and the current at the onset of significant fluid decrease.

FIGS. 4A, 4B and 4C show schematic plots of the alternating current I supplied by current source 30, and the resulting voltage drops and difference signal, as functions of time. The wave form of alternating current I shown in FIGS. 4A, 4B and 4C is a square wave. FIG. 4A shows the situation at the start of monitoring. Both $V_M$ and $V_R$ are substantially in phase with current I. Because the biological object has both an equivalent resistance and an equivalent capacitance, voltage drops $V_M$ and $V_R$ can not be exactly in phase with each other; but phase locking means 48 is used to synchronize the phases of the signals representative of $V_M$ and $V_R$, so that a suitable adjustment of variable resistor 26 substantially nulls the difference signal produced by subtraction means 40 and labeled in FIG. 4A as "$V_M$-$V_R$". FIG. 4B shows the situation at the onset of significant fluid buildup. Because of the buildup of electrically conductive fluid within the patient's thorax, the amplitude of $V_M$ decreases. Therefore, the difference signal "$V_M$-$V_R$" has a significant amplitude in FIG. 4B, and is substantially out of phase (180°) with the current I. If the amplitude of the difference signal exceeds a threshold, display means 46 compares the phases of the difference signal and the current I. If the difference signal is out of phase (180°) with the current I, then the large amplitude is indicative of a buildup of fluid, and display means 46 triggers an alarm.

FIG. 4C shows the situation at the onset of significant fluid decrease. I is the same in FIG. 4C as in FIGS. 4A and 4B. As in FIG. 4B, $V_R$ in FIG. 4C is similar, but not identical to, $V_R$ in FIG. 4A because of electrode drift. Because of the decrease in electrically conductive fluid, $V_M$ is larger in amplitude in FIG. 4C than in FIG. 4A. As in FIG. 4B, the difference signal "$V_M$-$V_R$" has a significant amplitude in FIG. 4C. Unlike the difference signal in FIG. 4B, the difference signal in FIG. 4C is substantially in phase (0°) with the current I.

Figure 5:
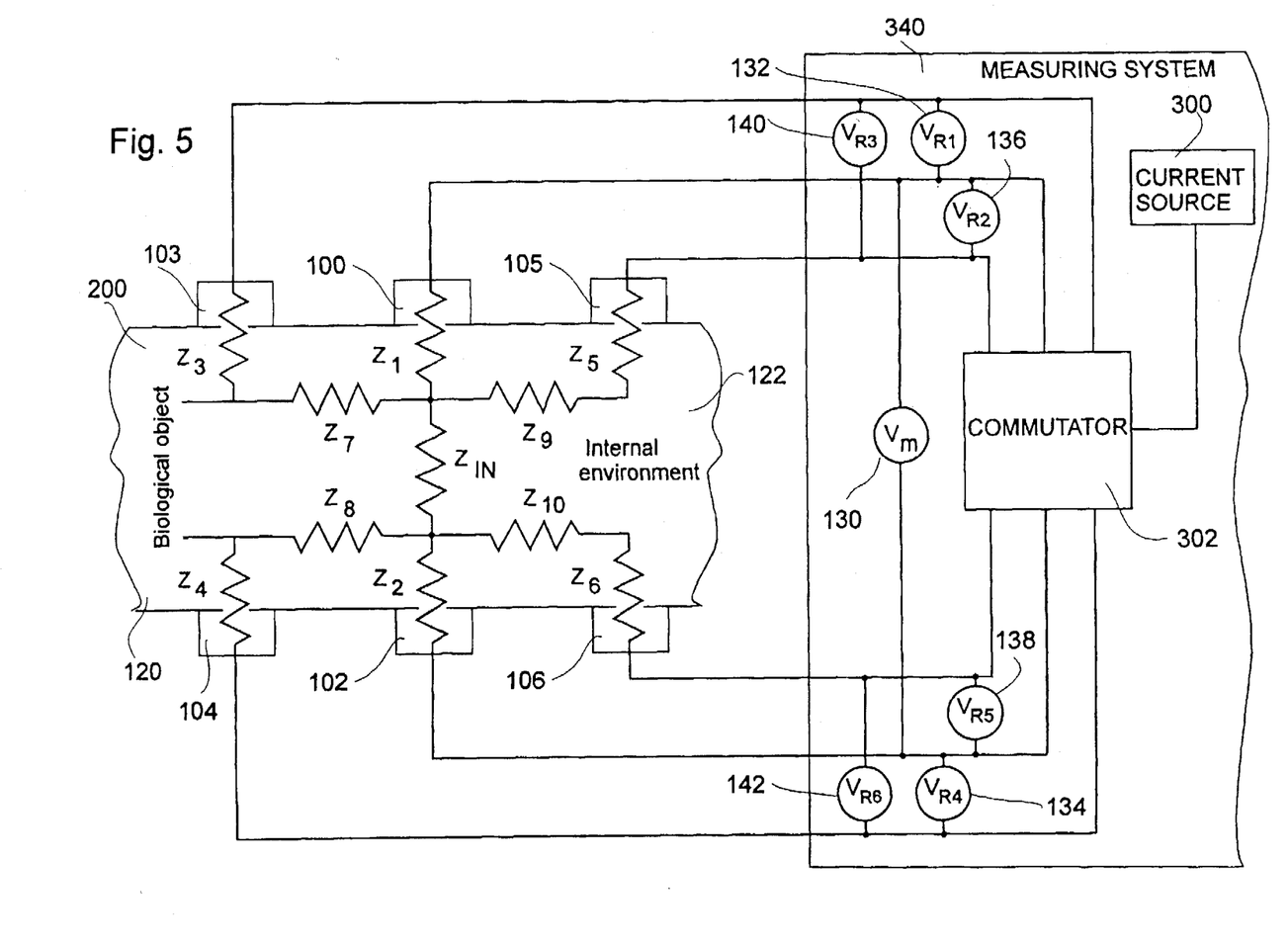
FIG. 5 is a schematic illustration of another preferred embodiment of a device according to the present invention.
Figure 6:
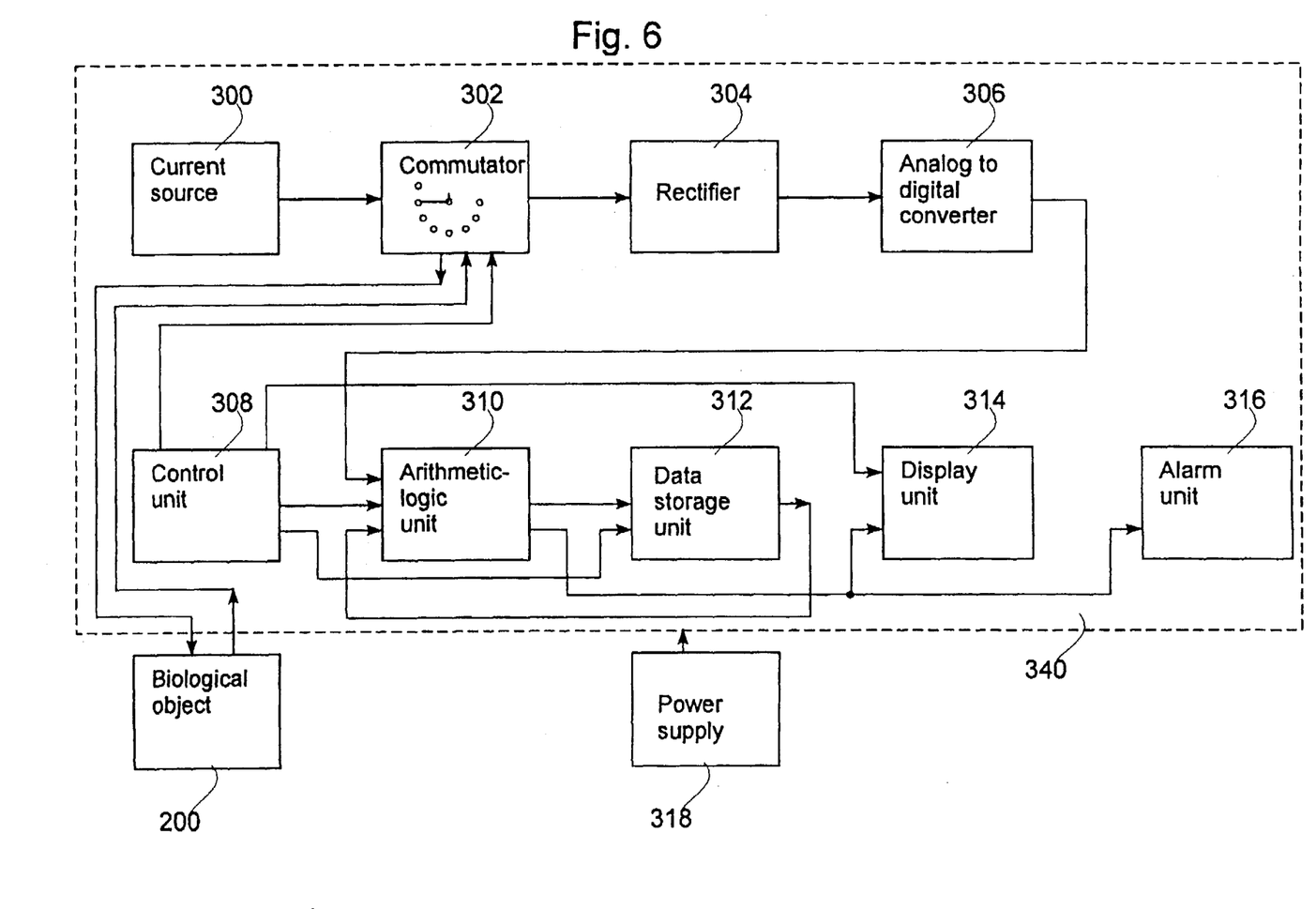
FIG. 6 is a schematic block diagram of the device shown in FIG. 5.
Figure 7A:
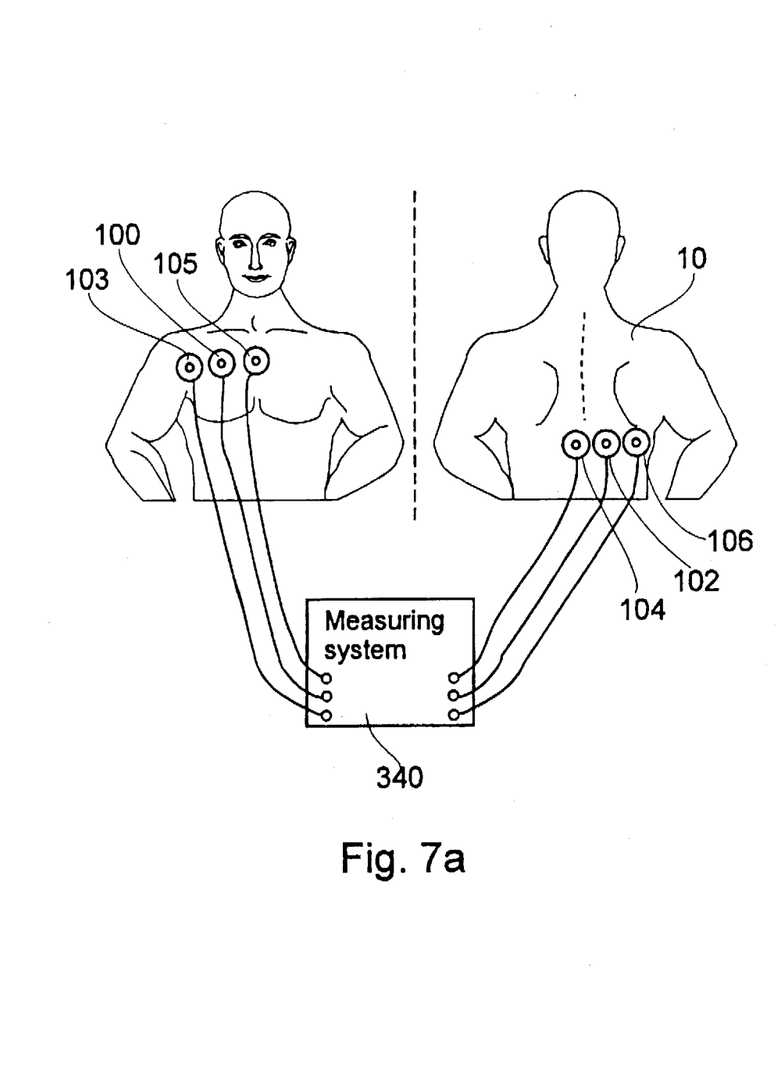
FIG. 7A is a schematic illustration of the device shown in FIG. 5 as used to monitor pulmonary edema.
Figure 7B:
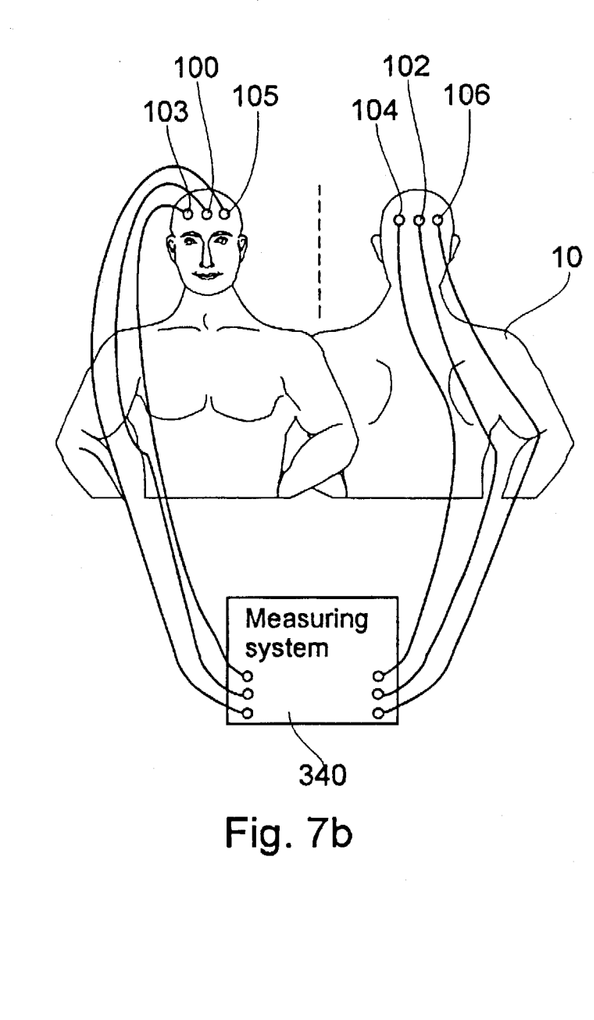
FIG. 7B is a schematic illustration of the device shown in FIG. 5 as used to monitor brain edema.

Another embodiment of a device according to the present invention is shown in FIGS. 5-7, wherein the actual value of the internal impedance $Z_{IN}$ of a biological 200, as well as changes in $Z_{IN}$, are determined.

As shown in the figures, a device according to the present invention includes a first measurement electrode 100 and a second measurement electrode 102 placed on opposite sides of a biological object 200. The reference electrodes, 103 and 105, are placed on opposite sides of measurement electrode 100, and two reference electrodes, 104 and 106, are placed on opposite sides of measurement electrode 102.

Preferably, a source 300 of alternating current supplies between about 1 mA and about 2 mA of current at a frequency of between about 50 Khz and about 200 Khz.

As shown in FIG. 5, biological object 200, electrodes 100 and 102, and current source 300 comprise a measurement circuit. Biological object 200, electrodes 100 and 103, and current source 300 comprise a first reference circuit. Biological object 200, electrodes 100 and 105, and current source 300 comprise a second reference circuit. Biological object 200, electrodes 103 and 105, and current source 300 comprise a third reference circuit. Biological object 200, electrodes 102 and 104, and current source 300 comprise a fourth reference circuit. Biological object 200, electrodes 102 and 106, and current source 300 comprise a fifth reference circuit. Biological object 200, electrodes 104 and 106, and current source 300 comprise a sixth reference circuit.

Voltage measurement means 130 is provided for measuring the voltage drop $V_M$ across the measurement circuit, $V_M$ being proportional to a total impedance of the biological object. Voltage measurement means 132, 136 and 140 are provided for measuring the voltage drops, $V_{R1}$, $V_{R2}$ and $V_{R3}$ across the first, the second and the third reference circuits, respectively. Voltage measurement means 134, 138 and 142 are provided for measuring the voltage drops, $V_{R4}$, $V_{R5}$ and $V_{R6}$ across the fourth, the fifth and the sixth reference circuits, respectively.

It is to be understood that the preferred embodiment of FIG. 5 is illustrative. In particular, the scope of the present invention is not restricted to circuitry in which voltage drops across the measurement circuit and the reference circuits are measured explicitly, but rather includes all circuitry which accomplishes the ends of the method of the present invention, using signals representative of the voltage drops $V_M$, $V_{R1}$, $V_{R2}$, $V_{R3}$, $V_{R4}$, $V_{R5}$ and $V_{R6}$, respectively.

As shown in FIG. 5, the impedance of the measurement circuit, which is the total impedance $Z_T$ of biological object 200, is the sum of the following impedances:

$Z_{IN}$—the internal impedance of biological object 200;

$Z_1$—which includes the impedance of electrode 100; the impedance of the skin-electrode contact of electrode 100; and a skin impedance;

$Z_2$—which includes the impedance of electrode 102; the impedance of the skin-electrode contact of electrode 102; and a skin impedance;

Thus, $$Z_{IN} = Z_T - Z_1 - Z_2$$

According to the present invention, $Z_1$ is calculated according to the impedances of the first, the second, and the third reference circuits, as follows:

$$Z_I = Z_1 + Z_7 + Z_3$$

$$Z_{II} = Z_1 + Z_9 + Z_5$$

$$Z_{III} = Z_3 + Z_7 + Z_9 + Z_5$$

Thus, $$Z_I + Z_{II} - Z_{III} = 2Z_1$$

Therefore $$Z_1 = (Z_I + Z_{II} - Z_{III})/2$$

Where:

$Z_I$—is the impedance of the first reference circuit;

$Z_{II}$—is the impedance of the second reference circuit;

$Z_{III}$—is the impedance of the third reference circuit;

$Z_1$—includes the impedance of electrode 100, the impedance of the skin-electrode contact of electrode 100, and a skin impedance;

$Z_3$—includes the impedance of electrode 103, the impedance of the skin-electrode contact of electrode 103, and a skin impedance; and $Z_5$—includes the impedance of electrode 105, the impedance of the skin-electrode contact of electrode 105, and a skin impedance;

$Z_7$—is the impedance of the skin between electrodes 100 and 103; and $Z_9$—is the impedance of the skin between electrodes 100 and 105.

Similarly, $Z_2$ is calculated according to the impedances of the fourth, the fifth, and the sixth reference circuits, as follows:

$$Z_{IV} = Z_2 + Z_8 + Z_4$$

$$Z_V = Z_2 + Z_{10} + Z_6$$

$$Z_{VI} = Z_4 + Z_8 + Z_{10} + Z_6$$

Thus, $$Z_{IV} + Z_V - Z_{VI} = 2Z_2$$

Therefore $$Z_2 = (Z_{IV} + Z_V - Z_{VI})/2$$

Where:

$Z_{IV}$—is the impedance of the fourth reference circuit;

$Z_V$—is the impedance of the fifth reference circuit;

$Z_{VI}$—is the impedance of the sixth reference circuit;

$Z_2$—includes the impedance of electrode 102, the impedance of the skin-electrode contact of electrode 102, and a skin impedance;

$Z_4$—includes the impedance of electrode 104, the impedance of the skin-electrode contact of electrode 104, and a skin impedance; and $Z_6$—includes the impedance of electrode 106, the impedance of the skin-electrode contact of electrode 106, and a skin impedance;

$Z_8$—is the impedance of the skin between electrodes 102 and 104; and $Z_{10}$—is the impedance of the skin between electrodes 102 and 106.

Thus, according to the present invention, the internal impedance $Z_{IN}$ of biological object 200 is calculated as follows:

$$Z_{IN} = Z_T - [(Z_I + Z_{II} - Z_{III})/2 + (Z_{IV} + Z_V - Z_{VI})/2]$$

Where $Z_T$, $Z_I$, $Z_{II}$, $Z_{III}$, $Z_{IV}$, $Z_V$ and $Z_{VI}$ are calculated according to Ohm's Law based on the measured values of $V_M$, $V_{R1}$, $V_{R2}$, $V_{R3}$, $V_{R4}$, $V_{R5}$ and $V_{R6}$, respectively.

The calculation of the actual impedance values of the skin-electrode contacts of measurement electrodes 100 and 102 enables to carry out long-term monitoring of the electrical impedance of a biological object with compensation for skin-electrode resistance drifts, even when the impedance values of the skin-electrode contacts are substantially different.

As shown in FIG. 6, a device according to the present invention includes a measuring system 340. Measuring system 340 preferably includes: current source 300; commutator 302 for alternately connecting current source 300 to a distinct electrical circuit; a rectifier 304 for obtaining the absolute value of the signals representing the voltage drops $V_M$, $V_{R1}$, $V_{R2}$, $V_{R3}$, $V_{R4}$, $V_{R5}$ and $V_{R6}$; an analog to digital converter 306 for converting the signals to a digital form; an arithmetic-logic unit 310 for carrying out calculations; a data-storage unit 312 for storing data during the monitoring period; a display unit 314; an alarm unit 316; and a control unit 308 for controlling the operation of commutator 302, arithmetic-logic unit 310, data storage unit 312, and display unit 314. Arithmetic-logic unit 310 is electrically connected to data-storage unit 312, display unit 314, and alarm unit 316. Measuring system 340 is powered by means of a power supplier 318.

When using a device according to the present invention, electrical source 300 is alternately connected to each of the electrical circuits shown in FIG. 5 by means of commutator 302. The signal representing the voltage drop of a specific electrical circuit is fed into rectifier 304 which provides the absolute value of such voltage drop. An analog to digital converter converts the obtained signal to a digital form. The obtained signal is fed into arithmetic logic unit 310 and stored in data-storage unit 312. Then, control unit 308 orders commutator 302 to connect electrical source 300 to the next electrical circuit.

After storage unit 312 has received data from each of the seven electrical circuits, arithmetic logic unit 310 calculates the internal impedance $Z_{IN}$ according to the method described above.

Preferably, the process described above is carried out periodically, so that arithmetic logic unit 310 simultaneously calculates the values of the internal impedance $Z_{IN}$ as well as changes in $Z_{IN}$. The change in $Z_{IN}$ may be calculated, for example, as the difference between the last value and the initial value or as a percentage from the initial value. The results of the calculations are transmitted to display unit 314, to data storage unit 312, and to alarm unit 316.

In the event that the value of $Z_{IN}$ has decreased below a critical value, and/or in the event that the change in $Z_{IN}$ has exceeded a critical value, the alarm unit is activated.

Data storage unit 312 may provide data for analysis during the monitoring period so as to monitor the progress of the disease.

FIG. 7a illustrates the use of a device according to the present invention as used to monitor pulmonary edema. Measurement electrodes 100 and 102 are placed on opposite sides of the thorax of a patient 10. Electrode 100 is placed at the point of intersection of the right 3-intercostal space and the right medroclavicular line of patient 10. Measurement electrode 102 is placed on the back of patient 10, at the point of intersection of the right 8-intercostal space and the right scapular line.

Reference electrodes 103 and 105 are placed on opposite sides of electrode 100, and reference electrodes 104 and 106 are placed on opposite sides of electrode 102. The electrodes are connected to measuring system 340.

A device according to the present invention may be used to monitor internal thoracic impedance for early detection of pulmonary edema as well as for monitoring the disease during treatment.

FIG. 7b illustrates the use of a device according to the present invention as used to monitor cerebral edema. Measurement electrodes 100 and 102 are placed on opposite sides of the head of patient 10. Reference electrodes 104 and 106 are placed on opposite sides of electrode 102. The electrodes are connected to measuring system 340. The device may be used to monitor internal impedance for early detection of cerebral edema as well as for monitoring the disease during treatment.

while the invention has been described with respect to a limited number of embodiments, it will be appreciated that many variations, modifications and other applications of the invention may be made.

What is claimed is:

1. A method for monitoring the internal electrical impedance of a biological object, with compensation for skin-electrode resistance drift, during an extended monitoring period, comprising the steps of:
   (a) placing a first measurement electrode and a second measurement electrode on the biological object, said first measurement electrode and said second measurement electrode being part of a measurement circuit;
   (b) placing a first reference electrode and a second reference electrode on the biological object, substantially adjacent to said first measurement electrode, said first measurement electrode and said first reference electrode being part of a first reference circuit, said first measurement electrode and said second reference electrode being part of a second reference circuit, said first reference electrode and said second reference electrode being part of a third reference circuit;
   (c) at least once during the monitoring period:
      (i) measuring a first electrical impedance of said measurement circuit;
      (ii) measuring a second electrical impedance of said first reference circuit;
      (iii) measuring a third electrical impedance of said second reference circuit; and
      (iv) measuring a fourth electrical impedance of said third reference circuit.

2. The method of claim 1, further comprising the step of: at least once during the monitoring period, calculating the value of the skin-electrode resistance drift of said first measurement electrode.

3. The method of claim 1, further comprising the steps of:
   (a) placing a third reference electrode and a fourth reference electrode on the biological object, substantially adjacent to said second measurement electrode, said second measurement electrode and said third reference electrode being part of a fourth reference circuit, said second measurement electrode and said fourth reference electrode being part of a fifth reference circuit, said third reference electrode and said fourth reference electrode being part of a sixth reference circuit;
   (c) at least once during the monitoring period:
      (i) measuring a fifth electrical impedance of said fourth reference circuit;
      (ii) measuring a sixth electrical impedance of said fifth reference circuit; and
      (iii) measuring a seventh electrical impedance of said sixth reference circuit.

4. The method of claim 1, wherein said first reference electrode and said second reference electrode are placed on opposite sides of said first measurement electrode.

5. The method of claim 4, further comprising the step of: at least once during the monitoring period, calculating the value of the skin-electrode resistance drift of said first measurement electrode according to:

$$Z_1 = (Z_I + Z_{II} - Z_{III})/2$$

where:

$Z_1$ is the skin-electrode resistance drift of said first measurement electrode;

$Z_I$ is said second electrical impedance;

$Z_{II}$ is said third electrical impedance; and $Z_{III}$ is said fourth electrical impedance.

6. The method of claim 5, further comprising the steps of:
   (a) placing a third reference electrode and a fourth reference electrode on the biological object, substantially adjacent to said second measurement electrode, said second measurement electrode and said third reference electrode being part of a fourth reference circuit, said second measurement electrode and said fourth reference electrode being part of a fifth reference circuit, said third reference electrode and said fourth reference electrode being part of a sixth reference circuit;
   (b) at least once during the monitoring period:
      (i) measuring a fifth electrical impedance of said fourth reference circuit;
      (ii) measuring a sixth electrical impedance of said fifth reference circuit; and
      (iii) measuring a seventh electrical impedance of said sixth reference circuit.

7. The method of claim 6, further comprising the step of: at least once during the monitoring period, calculating the value of the skin-electrode resistance drift of said second measurement electrode.

8. The method of claim 7, further comprising the step of: at least once during the monitoring period, calculating the value of the skin-electrode resistance drift of said second measurement electrode according to:

$$Z_2 = (Z_{IV} + Z_V - Z_{VI})/2$$

where:

$Z_2$ is the skin-electrode resistance drift of said second measurement electrode;

$Z_{IV}$ is said fifth electrical impedance;

$Z_V$ is said sixth electrical impedance; and $Z_{VI}$ is said seventh electrical impedance.

9. The method of claim 8, further comprising the step of: at least once during the monitoring period, calculating the internal electrical impedance of the biological object according to:

$$Z_{IN} = Z_T - (Z_1 + Z_2)$$

where:

$Z_{IN}$ is the internal electrical impedance of the biological object;

$Z_1$ is the skin-electrode resistance drift of said first measurement electrode;

$Z_2$ is the skin-electrode resistance drift of said second measurement electrode; and $Z_T$ is said first electrical impedance.

10. The method of claim 9, further comprising the step of: if the electrical impedance of the biological object decreases below a threshold value: initiating an emergency procedure.

11. The method of claim 9, wherein the electrical impedance of the biological object is calculated at least twice during the monitoring period.

12. The method of claim 11, further comprising the step of: if the change in the electrical impedance of the biological object exceeds a threshold value: initiating an emergency procedure.

13. A method for monitoring the internal electrical impedance of a biological object, with compensation for skin-electrode resistance drift, during an extended monitoring period, comprising the steps of:

(a) placing a first measurement electrode and a second measurement electrode on the biological object, said first measurement electrode and said second measurement electrode being part of a measurement circuit;

(b) placing a first reference electrode and a second reference electrode on the biological object, substantially adjacent to said first measurement electrode, said first measurement electrode and said first reference electrode being part of a first reference circuit, said first measurement electrode and said second reference electrode being part of a second reference circuit, said first reference electrode and said second reference electrode being part of a third reference circuit;

(c) at least once during the monitoring period:
  (i) imposing an alternating electrical current between said first measurement electrode and said second measurement electrode and obtaining a first voltage signal representative of a voltage drop in said measurement circuit;
  (ii) imposing an alternating electrical current between said first measurement electrode and said first reference electrode and obtaining a second voltage signal representative of a voltage drop in said first reference circuit;
  (iii) imposing an alternating electrical current between said first measurement electrode and said second reference electrode and obtaining a third voltage signal representative of a voltage difference in said second reference circuit;
  (iv) imposing an alternating electrical current between said first reference electrode and said second reference electrode and obtaining a fourth voltage signal representative of a voltage drop in said third reference circuit.

14. The method of claim 13, further comprising the steps of:

(a) placing a third reference electrode and a fourth reference electrode on the biological object, substantially adjacent to said second measurement electrode, said second measurement electrode and said third reference electrode being part of a fourth reference circuit, said second measurement electrode and said fourth reference electrode being part of a fifth reference circuit, said third reference electrode and said fourth reference electrode being part of a sixth reference circuit;

(b) at least once during the monitoring period:
  (i) imposing an alternating electrical current between said second measurement electrode and said third reference electrode and obtaining a fifth voltage signal representative of a voltage drop in said fourth reference circuit;
  (ii) imposing an alternating electrical current between said second measurement electrode and said fourth reference electrode and obtaining a sixth voltage signal representative of a voltage drop in said fifth reference circuit; and
  (iii) imposing an alternating electrical current between said third reference electrode and said fourth reference electrode and obtaining a seventh voltage signal representative of a voltage drop in said sixth reference circuit.

15. An impedance plethysmography device, comprising:

(a) a first measurement electrode;

(b) a second measurement electrode;

(c) a first reference electrode;

(d) a second reference electrode;

(e) a measurement electrical circuit including said first measurement electrode, said second measurement electrode, and a first impedance measurement means for measuring a first electrical impedance;

(f) a first reference electrical circuit including said first measurement electrode, said first reference electrode, and a second impedance measurement means for measuring a second electrical impedance;

(g) a second reference electrical circuit including said first measurement electrode, said second reference electrode, and a third impedance measurement means for measuring a third electrical impedance;

(h) a third reference electrical circuit including said first reference electrode, said second reference electrode, and a fourth impedance measurement means for measuring a fourth electrical impedance.

16. The device of claim 15, further comprising:

(a) a third reference electrode;

(b) a fourth reference electrode;

(c) a fourth reference electrical circuit including said second measurement electrode, said third reference electrode, and a fifth impedance measurement means for measuring a fifth electrical impedance;

(d) a fifth reference electrical circuit including said second measurement electrode, said fourth reference electrode, and a sixth impedance measurement means for measuring a sixth electrical impedance;

(e) a sixth reference electrical circuit including said third reference electrode, said fourth reference electrode, and a seventh impedance measurement means for measuring a seventh electrical impedance.

17. The device of claim 16, wherein said measurement electrical circuit, and said first, second, third, fourth, fifth and sixth reference electrical circuits share a common source of alternating electrical current.

18. The device of claim 17, further comprising a commutator element for alternately connecting said source of alternating current with said measurement circuit, and said first, second, third, fourth, fifth and sixth reference electrical circuits.

19. The device of claim 15, wherein said measurement electrical circuit, and said first, second and third reference electrical circuits share a common source of alternating electrical current.

20. The device of claim 19, wherein said alternating electrical current has a frequency of between about 50 Khz and about 200 Khz.

21. The device of claim 19, further comprising a commutator element for alternately connecting said source of alternating current with said measurement circuit, said first reference circuit, said second reference circuit, and said third reference circuit.

22. A medical monitoring system comprising an impedance plethysmography device, said impedance plethysmography device further comprising:

(a) a first measurement electrode;

(b) a second measurement electrode;

(c) a first reference electrode;

(d) a second reference electrode;

(e) a measurement electrical circuit including said first measurement electrode, said second measurement electrode, and a first impedance measurement means for measuring a first electrical impedance;

(f) a first reference electrical circuit including said first measurement electrode, said first reference electrode, and a second impedance measurement means for measuring a second electrical impedance;

(g) a second reference electrical circuit including said first measurement electrode, said second reference electrode, and a third impedance measurement means for measuring a third electrical impedance;

(h) a third reference electrical circuit including said first reference electrode, said second reference electrode, and a fourth impedance measurement means for measuring a fourth electrical impedance.

23. The medical monitoring system of claim 22, wherein said impedance plethysmography device further comprises:

(a) a third reference electrode;

(b) a fourth reference electrode;

(c) a fourth reference electrical circuit including said second measurement electrode, said third reference electrode, and a fifth impedance measurement means for measuring a fifth electrical impedance;

(d) a fifth reference electrical circuit including said second measurement electrode, said fourth reference electrode, and a sixth impedance measurement means for measuring a sixth electrical impedance;

(e) a sixth reference electrical circuit including said third reference electrode, said fourth reference electrode, and a seventh impedance measurement means for measuring a seventh electrical impedance.

* * * * *